United States Patent
Schwanke et al.

(10) Patent No.: US 10,024,775 B2
(45) Date of Patent: Jul. 17, 2018

(54) METHOD AND DEVICE FOR DETERMINING THE ABRASION PROPERTIES OF A COATED FLAT PRODUCT

(71) Applicant: ThyssenKrupp Steel Europe AG, Duisburg (DE)

(72) Inventors: Heinz-Gunter Schwanke, Oberhausen (DE); Klaus Uran, Moers (DE); Robert Yanik, Paderborn (DE); Thomas Huper, Moers (DE)

(73) Assignee: ThyssenKrupp Steel Europe AG, Duisburg (DE)

( * ) Notice: Subject to any disclaimer, the term of this patent is extended or adjusted under 35 U.S.C. 154(b) by 110 days.

(21) Appl. No.: 15/022,740

(22) PCT Filed: Sep. 18, 2013

(86) PCT No.: PCT/EP2013/069407
§ 371 (c)(1),
(2) Date: Mar. 17, 2016

(87) PCT Pub. No.: WO2015/039685
PCT Pub. Date: Mar. 26, 2015

(65) Prior Publication Data
US 2016/0231218 A1    Aug. 11, 2016

(51) Int. Cl.
*G01N 3/56* (2006.01)
*G01N 19/04* (2006.01)

(52) U.S. Cl.
CPC ............... *G01N 3/56* (2013.01); *G01N 19/04* (2013.01)

(58) Field of Classification Search
None
See application file for complete search history.

(56) References Cited

U.S. PATENT DOCUMENTS

| | | | | |
|---|---|---|---|---|
| 4,188,824 | A | * 2/1980 | McCarthy | G01N 19/04 73/1.01 |
| 5,019,460 | A | * 5/1991 | Yasuda | C23C 2/06 427/123 |

(Continued)

FOREIGN PATENT DOCUMENTS

| | | |
|---|---|---|
| CA | 2006756 C | 6/1994 |
| DE | 20010467 U1 | 9/2000 |

(Continued)

*Primary Examiner* — Jill Culler
(74) *Attorney, Agent, or Firm* — The Webb Law Firm (57) ABSTRACT

A method for determining the abrasion properties of a coated flat product is described. A corresponding method is proposed in which an adhesive strip is stuck to the coating of the flat product, the flat product is bent in the region provided with the adhesive strip or to be provided with the adhesive strip, the adhesive strip after bending is peeled off together with abrasion material of the coating adhering to the adhesive strip, the grey tones of the adhesive strip are determined stripe by stripe crossways to the width of the abrasion, and on the basis of the grey tones determined stripe by stripe the grey width is determined as the width of the abrasion and/or the representative grey tone is determined as the representative grey tone of the grey tones determined stripe by stripe.

19 Claims, 4 Drawing Sheets

(56) References Cited

U.S. PATENT DOCUMENTS

| | | | | |
|---|---|---|---|---|
| 5,049,453 | A | * 9/1991 | Suemitsu | B32B 15/013 |
| | | | | 148/533 |
| 5,649,447 | A | * 7/1997 | Van Avery | G01N 19/04 |
| | | | | 73/150 A |
| 7,294,412 | B2 | * 11/2007 | Takada | C21D 8/0273 |
| | | | | 148/320 |
| 2006/0124907 | A1 | 6/2006 | Takada et al. | |
| 2008/0083477 | A1 | 4/2008 | Drillet et al. | |
| 2012/0201470 | A1 | 8/2012 | Pekar et al. | |

FOREIGN PATENT DOCUMENTS

| | | |
|---|---|---|
| DE | 102011010315 A1 | 8/2012 |
| EP | 0104369 A2 | 4/1984 |
| JP | S60125617 A | 7/1985 |
| JP | S62100646 A | 5/1987 |
| JP | 200064013 A | 2/2000 |
| JP | 2007225518 A | 9/2007 |
| JP | 2011127216 A | 6/2011 |
| JP | 5513148 B2 | 6/2014 |
| KR | 1020070003366 A | 1/2007 |
| KR | 1020120074144 A | 7/2012 |
| WO | 9627977 A1 | 9/1996 |
| WO | 2004063410 A1 | 7/2004 |

* cited by examiner

METHOD AND DEVICE FOR DETERMINING THE ABRASION PROPERTIES OF A COATED FLAT PRODUCT

CROSS-REFERENCE TO RELATED APPLICATIONS

This application is the United States national phase of International Application No. PCT/EP2013/069407 filed Sep. 18, 2013, the disclosure of which is hereby incorporated in its entirety by reference.

BACKGROUND OF THE INVENTION

Field of the Invention

The present invention relates to a method for determining the abrasion properties of a coated flat product, preferably a metal flat product, in particular a galvanised steel flat product. In addition the invention relates to a device for determining the abrasion properties of such a coated flat product.

Description of Related Art

For many applications an essential property of coated flat products is the abrasion resistance of the coating. Therefore in the manufacture of corresponding flat products stringent requirements are placed on the abrasion tendency of the coating. Coated flat products are understood to include in particular metal, steel, light metal or composite flat products, wherein these may exist for example as strip, sheet metal, blank or plate bar materials. Furthermore these products may preferably be hot-rolled or cold-rolled products. As regards the coating, zinc coatings for example are suitable, which can be produced by hot dip galvanising or electrolytic galvanising of for example a steel flat product.

On account of the stringent requirements placed on the coating of corresponding flat products it is very important for the purposes of quality assurance to be able to determine the abrasion properties in a reproducible and quantifiable manner. Galvannealed coated steel strips, which are both galvanised and annealed, are used for example in the automobile industry as body panel parts, reinforcements or internal parts and must therefore satisfy high surface requirements. Here so-called powdering can be a problem, which describes a type of abrasion of the zinc coating that occurs during shaping, in which particles of the coating break off. This is typically distinguished from flaking, which is an area-type delamination of the coating.

The tendency of a coated flat product to exhibit powdering can be assessed with the so-called adhesive strip bending test. In this test an adhesive strip is stuck to a workpiece sample which is strongly bent in the region of the adhesive strip, normally resulting in a powdering. The broken off particles of the coating remain on the adhesive strip, which is pulled off after the bending, generally only after the workpiece has been bent back (flattened) to the original state. The adhesive strip is then stuck onto a white background so that the particles of the coating show up as a grey covering. If the bending has taken place along a bending line, the broken off particles are also present in the form of a line. The degree of powdering is determined on the basis of the blackening of the line by the particles of the coating or on the basis of the width of the line of particles of the coating. Since the blackening varies in a direction crossways to the bending line and slowly tails off in the direction of the edges, the determination of the blackening or the width of the line is to a high degree subjective.

In addition methods such as the double Olsen test, the cupping test, the hat profile test or the strip tensile test are known. These methods however also do not provide satisfactory results, since they are generally not very reproducible. Furthermore the testable flat products may be limited as regards their thickness and strength.

SUMMARY OF THE INVENTION

An object of the present invention is therefore to elaborate and develop the method and the device of the type mentioned in the introduction and described in more detail hereinbefore so that the abrasion properties of a coated flat product can be characterised in a more objective, meaningful and reproducible manner.

This object is achieved by a method in which an adhesive strip is stuck to the coating of the flat product, in which the flat product is bent in the region provided with the adhesive strip or to be provided with the adhesive strip, in which the adhesive strip after the bending is pulled off together with abraded material of the coating adhering to the adhesive strip, in which the grey tones of the adhesive strip are determined stripe by stripe crossways to the width of the abrasion forming an abrasion mark, and in which on the basis of the grey tones determined stripe by stripe the grey width is determined as the width of the abrasion mark and/or the representative grey tone of the abrasion mark.

In addition this object is achieved by a device in which a detection unit, in particular an image processing device, is provided for the stripe by stripe determination of grey tones of an adhesive strip and/or a representation of an adhesive strip crossways to the width of abrasion forming an abrasion mark adhering to the adhesive strip, and that a determination means is provided for determining the grey width as the width of the abrasion mark and/or of the representative grey tone of the abrasion mark on the basis of the grey tones determined stripe by stripe.

Preferably the adhesive strip is stuck to the flat product before the bending operation, though this can however also take place subsequently, although in this case the danger is greater that not all abrasion material undergoes analysis since this is not completely taken up by the adhesive strip. Preferably the flat product can be flattened after the bending and thus bent back and substantially restored to the initial state. The abrasion is thus more able to take place. The adhesive strip should however already be applied before the flattening.

According to the invention the adhesive strip or the longitudinal track or mark of the abrasion material adhering to the adhesive strip is therefore investigated stripe by stripe and not as a whole. In addition the stripe by stripe investigation takes place crossways to the width of the abrasion mark. Thus, many individual values as regards the grey tone are measured crossways to the abrasion mark, wherein the evaluation can in principle be carried out more accurately the more stripes are investigated crossways to the abrasion mark.

On the basis of the grey tones determined for the individual stripes a representative grey tone for the whole abrasion mark can now be determined for example. This representative grey tone is a measure of the abrasion properties of the coating. The higher the representative grey tone, the more the coating will tend to undergo powdering. By evaluating many individual stripes there is therefore less chance of a subjective erroneous assessment since individual stripes appear particularly dark or extremely bright. Alternatively or in addition to the representative grey tone the grey width, i.e. the width of the abrasion mark caused by the particles of the coating, can also be determined purely objectively from the grey tones of the individual stripes. On the basis of the grey tones of the individual stripes it is thus for example clearer where the abrasion mark begins and ends in a direction crossways to the latter and how wide the abrasion mark actually is. In other words the abrasion mark can be distinguished more easily from dirt particles that adhere to the coated flat product independently of the bending of the latter.

A further improvement of the reproducibility is achieved if the grey tones are not simply determined at several points crossways to the abrasion mark are in fact not necessarily constant. A representative grey tone determination is therefore carried out, which takes into account the variation of the grey tones along individual stripes. This preferably takes place by determining the grey tones along individual stripes. Individual very dark or very bright sections along a stripe or along several stripes therefore do not noticeably falsify the determination of the abrasion properties. It is however also possible to integrate the grey tones along the stripes or use another way of summating the grey tones.

In addition an improvement of the determination of the abrasion properties is achieved if the grey tones along the individual stripes of the abrasion mark on the adhesive strip are not determined subjectively by the human eye, but by a detection unit suitable for this purpose. In this way an objectivisation of the evaluation of the abrasion mark is ultimately achieved. Light-sensitive sensors for example are suitable for this purpose. The evaluation can however also be carried out using an image processing device. The image processing device can evaluate the abrasion mark directly or can evaluate a representation of the abrasion mark or of the adhesive strip. In the case of the direct evaluation of the abrasion mark this can be scanned by means of a scanner. Alternatively a representation of the abrasion mark can also be scanned, although this is in principle more complicated and susceptible to error. For example a digitised recording of the abrasion mark or of the adhesive strip, preferably in a known image format, is suitable as representation of the abrasion mark or adhesive strip. The recording can be produced by a camera, preferably a digital camera. The determination means for determining the grey width and/or the representative grey tone can in particular be a computer-based determination means, which performs a software-based evaluation of the grey tones.

It is understood in the present context that in particular a reproducible comparison of grey tones and/or a reproducible evaluation of grey tones of the abrasion mark measured stripe by stripe is desirable. Therefore in order to determine the representative grey tone it is preferred according to the invention to obtain average grey tones in the detection of the grey tones of the abrasion mark stripe by stripe as well as in the determination of an overall representative grey tone of the abrasion mark from the grey tones determined stripe by stripe. In principle the representative grey tones along the stripes and/or crossways to the abrasion mark could also be integrated or determined in another way.

The coated flat product is in particular a metal, steel, light metal and/or composite flat product, which may exist for example as strip, sheet material, blank or plate bar material. The flat product can be hot-rolled or cold-rolled. Also, a hot dip galvanised steel flat product is preferred. In particular a galvannealed steel sheet is preferred. The abrasion is thus preferably an abrasion of a galvanised layer, in particular a so-called powdering. The galvanised layer is furthermore in particular a zinc-iron layer.

The bending of the coated flat product is preferably carried out by bending the flat product in a V-shape along a longitudinal bending line. For this purpose the flat product is bent preferably using a bending wedge with a longitudinal bending edge, if necessary interrupted in some sections. The flat product can then be bent flat again.

With regard to the adhesive strip it is preferred if the abrasion forms a contrast to the adhesive strip and is thus sufficiently clearly distinguished from the adhesive strip. It is particularly preferred in this connection if the adhesive strip is substantially transparent. For a better contrast the surface of the initial sample of the flat product can also be cleaned by means of ethanol or with another cleaning agent.

Preferred realisations of the method and of the device are described together hereinafter, without however explicitly distinguishing between the method and the device. The preferred method and device features will however be obvious to the person skilled in the art from the context.

In a first preferred realisation of the invention it is envisaged that a grey tone pattern in the direction of the width of the abrasion or of the abrasion mark is created from the measured grey tones of the stripes. For this purpose the device can comprise a means for creating a grey tone pattern. The creation of the grey tone pattern can be performed using suitable software. With the aid of the corresponding grey tone pattern the grey width can then be determined in a properly reproducible manner as the width of the grey tone pattern and thus of the abrasion mark, and/or the representative grey tone can be determined as the representative grey tone of the grey tone pattern and thus of the abrasion mark.

In addition, with regard to the reproducibility and validity of the determined characteristic value for characterising the abrasion properties it is expedient if on the basis of the grey tone pattern the grey width is determined as the width of the grey tone pattern exceeding the grey tone limit value and/or the representative grey tone is determined as the representative grey tone of all grey tones exceeding the grey tone limit value. In this way grey tones that are not due to the abrasion but for example to a contamination of the investigated sample of the flat product can by and large be prevented from affecting the evaluation.

The grey tone limit value can in this connection be predetermined manually, and more specifically for example with the aid of empirical characteristic values. The grey tone limit value is however preferably specified on the basis of the respective grey tone pattern to be evaluated, for example by a means for determining the grey tone limit value. In this connection the grey tone limit value can be determined with the aid of the gradients of the grey tone pattern. For example, the grey tone limit value can be fixed at a value at which there is a sharp jump in the grey tone pattern. In principle however it is preferred if the grey tone limit value is automatically determined on the basis of the respective grey tone pattern to be evaluated, and more specifically for example based on software, according to corresponding preset values.

For an uncomplicated characterisation of the abrasion properties of a coating it is appropriate to determine a representative, in particular mean or integral, stripe grey tone for each stripe. The same procedure can alternatively or in addition be employed to determine the representative grey tone for the abrasion stripe as such based on the grey tones of the individual stripes.

A simple, accurate and preferably automated determination of the grey tones of individual stripes can be carried out photometrically, and more specifically either preferably directly or with the aid of a digitised record of the adhesive stripe by an image processing device. Image processing devices and if necessary appropriate software solutions for the corresponding image processing are already in principle known from the prior art and do not need to be described in particular at this point.

To evaluate the adhesive strip at least one, preferably digitised, recording can be generated from the adhesive strip. The grey tones can then be determined stripe by stripe on the basis of the at least one recording, and more specifically in particular by an image processing device as mentioned hereinbefore. The recording can in this case preferably take place from the adhesive strip illuminated in transmitted light or incident light. Transmitted light means that the adhesive strip is illuminated from the side of the adhesive strip facing away from the camera. Incident light means on the other hand that the illumination of the adhesive strip takes place from the same side from which the camera makes the recording from the adhesive strip.

The quality of the evaluation can in principle be increased if several recordings from the adhesive strip are taken and these recordings are superimposed so as to improve the contrast and the depth of sharpness for a new representation. The recordings can in this connection take place with different illumination times, in which individual recordings may be overexposed and/or underexposed. The recordings can alternatively or in addition also be distinguished by the fact that some recordings are produced by illumination in transmitted light and some by illumination in incident light.

Alternatively or in addition, for a more accurate evaluation of the adhesive strip this can be scanned stripe by stripe in order to determine grey tones crossways to the width of the abrasion, in particular of the abrasion mark. In this case therefore it is not the whole stripe as such that is detected, but the determination of the grey tone takes place in steps along the stripe. The stripe by stripe scanning can in this be performed if necessary by a commercially available scanner, which scans the adhesive strip or a representation of the adhesive strip stripe by stripe or, referred to the scanner, line by line and assigns a representative grey tone to each line.

In order to improve the reproducibility and validity of the evaluation the grey tones can be determined from at least 20 stripes, preferably at least 50 stripes, in particular at least 100 stripes, crossways to the width of the abrasion, in particular of the abrasion mark.

It has also been found that good evaluation results can be obtained if the grey tone limit value is 10%-40%, preferably 15%-35%, in particular 20%-30% of the value range from the minimum grey tone to the maximum grey tone. For example, the grey tone determination can be based on a scale that extends from 0 for black to 255 for pure white. In this case it is preferred if the grey tone limit value is chosen between 160 (37%) and 24 (6%), preferably between 170 (33%) and 220 (14%), in particular around 180 (29%).

With galvannealed steel flat products there is a connection between the iron content of the galvanised coating and the powdering tendency of the coating, such that the powdering tendency increases with the iron content of the galvanised coating. In this connection the galvanised coating has in principle a higher iron content the more strongly and longer the flat product is annealed. Accordingly it may be appropriate to employ this connection for a coated flat product to be investigated, in which the grey width and/or the representative grey tone is determined depending on the iron content of the coating. This can take place in particular for a constant grey tone limit value or independently of one another for different grey tone limit values. Thus, for example, it can be established or checked on the basis of the at least one determined correlation of the grey tone limit value whether a grey tone limit value leads to plausible results. Ideally the pairs of values of grey width and/or representative grey tone with and/or representative grey tone to iron content determined for the at least one grey tone limit value or the specific grey tone limit value should produce a good correlation and a plausible curve shape.

Preferably the iron content of a flat product sample can be determined on the basis of the dependence, determined once for a coated flat product, of grey tone width and/or representative grey tone on iron content, which were preferably determined for a constant grey tone limit value or separately for different grey tone limit values. In addition to this it is then simply necessary to determine the grey width and/or the representative grey tone. It therefore becomes possible from the evaluation also to draw a conclusion about the iron content. Then either the grey width and/or the mean grey tone or however the iron content directly can then be specified as the quantity determining the abrasion properties.

If the dependence and the correlation of grey tone width and/or representative grey tone on iron content is determined for different grey tone limit values, from this a preferred grey tone limit value can be obtained for determining the grey tone width and/or the representative grey tone of corresponding flat products. In this case preferably the grey tone limit value is chosen in which the pairs of values of grey width and/or the representative grey tone on the one hand and the iron content on the other hand have a pattern that is as plausible as possible and correlate as best as possible way to this pattern. With a poor correlation measurement value clusters are obtained that can be approximated only very imprecisely by a compensating curve. In the case of a good correlation all measurement values lie very close to a compensation curve, in particular a compensation straight line, which accordingly approximates very closely to the measurement values.

Alternatively or in addition for specific coated flat products not only the grey width and/or the representative grey tone, but also the iron content, can be determined, for example analytically. On the basis of the dependence, determined once for a coated flat product, of grey width and/or representative grey tone on the one hand to iron content of the other hand, which is preferably determined for a constant grey tone limit value or separately for different grey tone limit values, it can then be checked how the corresponding measurement value agrees with the corresponding dependence. This can be expressed by a characteristic value for the correlation of the pair of values with the previously determined mathematical dependence. If the characteristic value indicates too large a deviation from the previously determined dependence, intervention must be made if necessary or a renewed calibration must be carried out. Furthermore, preferably the characteristic value is not found for each measurement but instead a certain number of successive measurements are carried out so that no excessive relevance is accorded to individual outliers.

The characteristic value for the correlation may be used for example for the purpose of quality assurance with regard to the determination of the abrasion properties of a coated flat product. Thus evidence can be adduced if necessary to show that the determination of the abrasion properties is carried out with sufficient accuracy and reproducibility. For example the characteristic value can for this purpose be compared with a predetermined characteristic value limit. If the deviation is larger than the predetermined value, this can be indicated and/or displayed. This can serve for the purpose of performing a corresponding intervention or a renewed calibration. Alternatively or in addition the determined grey width and/or the representative grey tone can also be combined with additional information indicating that the significance of the corresponding values is reduced.

BRIEF DESCRIPTION OF THE DRAWINGS

The invention is described in more detail hereinafter with the aid of a drawing simply illustrating one exemplary embodiment, and with reference the drawings, in which.

DETAILED DESCRIPTION OF THE INVENTION

Figure 1:
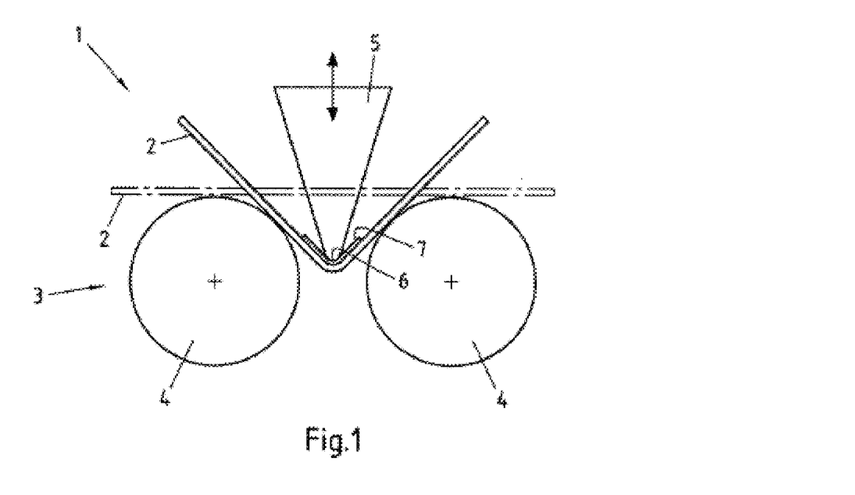
FIG. 1 is a detail of a device according to the invention for determining the abrasion properties of a coated flat product.

FIG. 1 shows a detail of a device 1 for bending a coated flat product 2. The device 1 comprises a so-called roller forming die 3 with two bending rollers 4 spaced apart from one another via a gap and a bending wedge 5 of V-shaped cross section and with a longitudinal edge 6. A coated flat product 2, on whose upper side an adhesive strip 7 has been applied, is positioned on the bending rollers 4. The bending wedge 5 can now be lowered into the gap between the bending rollers 4. The bending wedge 5 now presses with its edge 6 in the longitudinal direction on the adhesive strip 7 stuck to the flat product 2, whereby the flat product 2 is bent downwardly in the form of a V along a bending line defined by the edge 6 of the bending wedge 5. In FIG. 1 the flat product 2 is shown in the original position by dotted lines and in the bent position by continuous lines. After the coated flat product 2 has been bent the bending wedge 5 is raised and the flat product 2 is bent back and flattened again by a flattening device, not shown.

Figure 2:
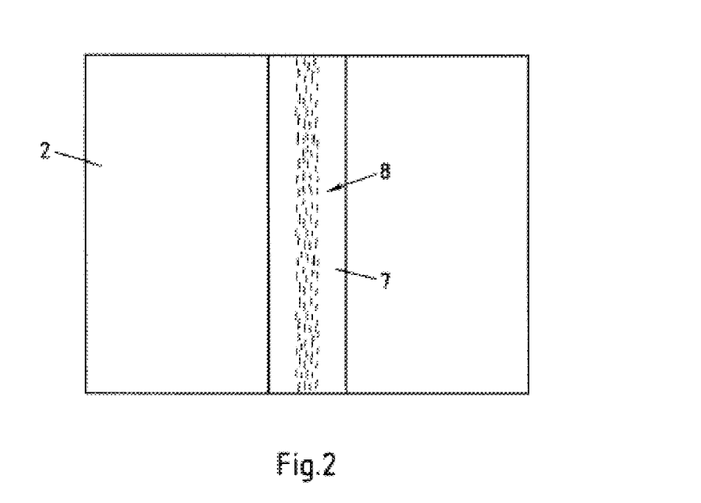
FIG. 2 is a plan view of a coated flat product with an adhesive strip for carrying out the method according to the invention for determining the abrasion properties.

The flat product 2 is shown in plan view from above in FIG. 2 in the bent-back and flattened state. Particles of the coating broken off along the bending line of the flat product 2 as a result of the powdering occurring during bending are schematically illustrated, and are identified as the abrasion mark 8. The adhesive strip 7 is peeled off to evaluate the coated flat product 2, the broken-off particles of the coating remaining as abrasion on the adhesive strip 7. Records are then taken of the adhesive strip 7 by means of a digital camera. For this, the adhesive strip 7 is illuminated from the same side as the images are taken (incident light) as well as from the opposite side (transmitted light). During each of the two illumination situations differently illuminated records are produced, which in some cases are overexposed and in some cases underexposed. A representation with increased contrast or depth of sharpness is then generated by software from the adhesive strip 7 by superposing all the generated images.

Figure 3:
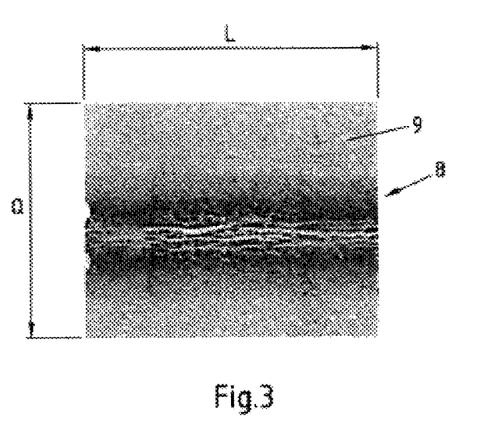
FIG. 3 shows the adhesive strip with an abrasion mark from FIG. 2.

The representation 9 of the adhesive strip 7 reproduced in FIG. 3 is then analysed in an image processing device. For this, the representation 9 of the adhesive strip 7 is scanned stripe by stripe and specifically in each case in a direction along the representation 9 of the adhesive strip 7 and the abrasion mark 8 that is parallel to the double arrow L. In this way a grey tone of the abrasion mark 8 is determined stripe by stripe. The grey tone of each stripe is at the same time averaged over its length, so that for each stripe a grey tone is obtained in the form of an averaged grey tone. Then on the basis of the averaged grey tones of the individual stripes a grey tone pattern 10 is generated crossways to the abrasion mark in the manner of a histogram. The direction crossways to the abrasion mark is symbolised by the double arrow Q.

Figure 4:
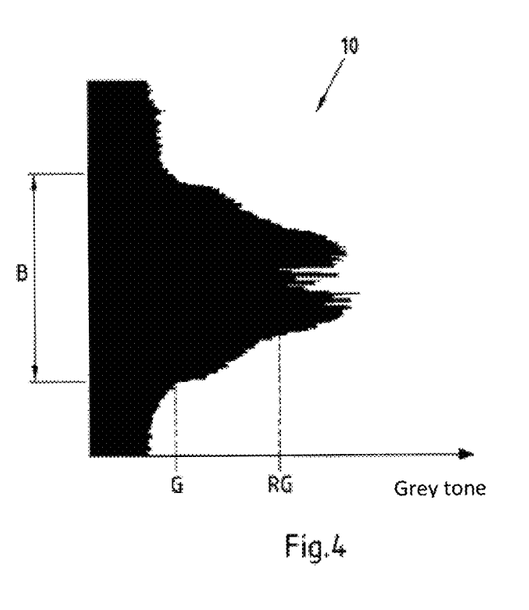
FIG. 4 is a histogram of the pattern of the grey tones of individual stripes crossways to the abrasion mark of the adhesive strip from FIG. 3.

The grey tone pattern 10 in the form of the histogram is illustrated in FIG. 4, in which each stripe is represented by a bar in histogram. The scanned stripes have like the bars a constant width. The longer a bar is, the darker is the representative grey tone for the corresponding stripe. This is illustrated on the X-axis, on which the grey tone is plotted. It can clearly be seen that the stripes in the middle of the adhesive strip 7 are darker than at the edge of the adhesive strip 7. The edges of the adhesive strip 7 are illustrated at the top and bottom in the grey tone distribution 10. In the grey tone pattern 10 the grey tones therefore increase slowly viewed from the edges. Starting at a specific grey tone there is however a sharp jump compared to the previous rise. This grey tone is defined as the grey tone limit value G. Only average grey tones of the grey tone pattern 10 that are greater than the grey tone limit value G are taken into account. The width of the grey tone pattern 10 for the grey tones that are larger than the grey tone limit value are now determined. This width is the grey width B of the abrasion mark 8 on the adhesive strip 7. In addition the values of all mean grey tones that are larger than the grey tone limit value G are averaged. The resulting mean grey tone is the representative grey tone RG of the abrasion mark 8. The representative grey tone RG and the grey width B represent in each case separately and jointly reproducible characteristic values for the abrasion properties of the investigated coated flat product 2.

Figure 5:
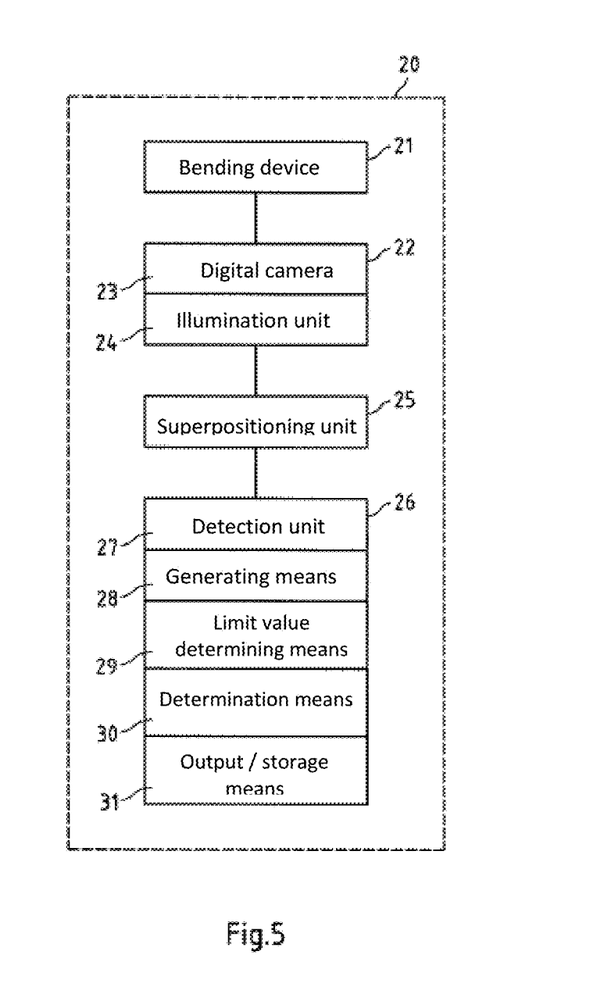
FIG. 5 is a schematic representation of the device for determining the abrasion properties of a coated flat product.

The arrangement 20 for carrying out the afore-described method for determining the abrasion properties of a coated flat product 2 is illustrated schematically in FIG. 5. The arrangement 20 comprises a bending device 21 according to FIG. 1 for bending a coated flat product 2 and for the subsequent flattening, in order to produce in reproducible manner abrasion that remains adhering to an adhesive strip 7. The arrangement 20 furthermore comprises a device 22 for generating a representation 9 of the adhesive strip 7 comprising a digital camera 23 and an illumination unit 24 for illuminating the adhesive strip 7 while the digital camera 23 generates records from the adhesive strip 7. In addition a superpositioning unit 25 is provided for superimposing the recordings to produce a very contrast-rich representation 9 of the adhesive strip 7. This representation 9 serves as a reference for the device 26 for determining the abrasion properties of a coated flat product 2. This device 26 comprises a detection unit 27 in the form of an image processing device. This scans the representation 9 of the adhesive strip 7 stripe by stripe and determines a representative grey tone for each stripe. A generating means 28 generates from the representative grey tones of the stripes a grey tone pattern 10 crossways to the abrasion mark 8 of the adhesive strip 7. In addition a limit value determining means is provided for determining a grey tone limit value G on the basis of the grey tone pattern 10. Apart from this a determination means 30 is also present for determining the grey width and/or the representative grey tone on the basis of the grey tone pattern 10, as well as an output and storage means 31 for outputting and storing the determined values for the grey width and the representative grey tone.

In the illustrated and in this respect preferred method and the corresponding device the representative grey width is specified in mm and the grey tone is given as a value between 0 for completely dark and 255 for completely white. Other dimensional units are however possible.

Figure 6:
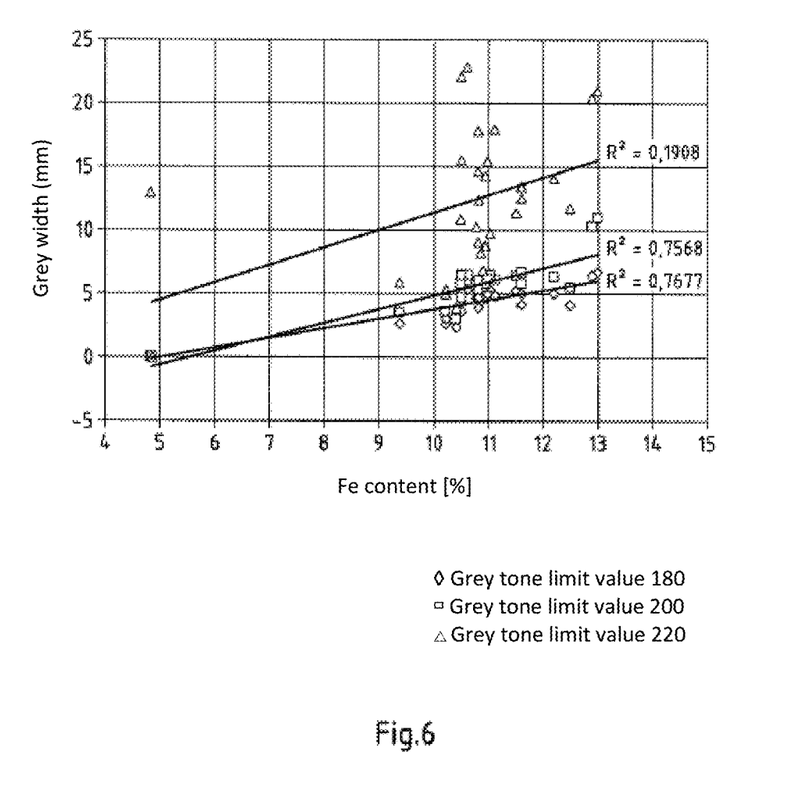
FIG. 6 is a graphical representation of the functional connection between grey tone width and iron content of a coated flat product.

FIG. 6 shows a diagram on which the iron content of the coating is plotted on the X-axis and the grey width on the Y-axis. Grey widths that have been determined depending on the iron content for specific grey tone limit values (180, 200 and 220) are plotted on the diagram. A straight line has been drawn approximating to the measurement values for each grey tone limit value, where in each case the quality of the correlation ($R^2$) of the best fit straight line with the measurement values is given. It can be seen in this case that the correlation is highest for a grey tone limit value of 180 ($R^2=0.7677$). Accordingly the grey tone limit value of 180 can be used for the later evaluation of flat products of the same type, so as to obtain results that are reproducible as possible. Since the abrasion correlates with the iron content, grey tone limit values that reproduce this correlation particularly well provide particularly significant and reproducible results.

The invention claimed is:

1. A method for determining the abrasion properties of a coated flat product comprising:
   sticking an adhesive strip to the coating of the flat product,
   bending the flat product in a region provided with the adhesive strip or to be provided with the adhesive strip,
   removing the adhesive strip after the bending together with abrasion material of the coating adhering to the adhesive strip, such that an abrasion mark is formed on the adhesive strip,
   scanning, by at least one scanner in communication with at least one processor, the adhesive strip or a representation of the adhesive strip to generate a scanned image,
   measuring, by the at least one processor, an average grey tone of each of a plurality of stripes of the scanned image, each of the plurality of stripes being oriented crossways to a width of the abrasion mark,
   determining, by the at least one processor, on the basis of the grey tones of the plurality of stripes, a grey width as the width of the abrasion mark and/or determining, by the at least one processor, a representative grey tone as the representative grey tone of the abrasion mark.

2. The method according to claim 1 comprising, generating from the average grey tones of the plurality of stripes of the scanned image, a grey tone pattern in the direction of the width of the abrasion mark and determining on the basis of the grey tone pattern the grey width as the width of the grey tone pattern and/or determining the representative grey tone as the representative grey tone of the grey tone pattern.

3. The method according to claim 2 comprising, determining on the basis of the grey tone pattern the grey width as the width of the grey tone pattern exceeding a grey tone limit value and/or determining the representative grey tone as the representative grey tone of all grey tones exceeding the grey tone limit value.

4. The method according to claim 2 comprising, fixing the grey tone limit value on the basis of the grey tone pattern.

5. The method according to claim 1 comprising, determining a mean or integral stripe grey tone for each stripe.

6. The method according to claim 1, wherein the measurement of the average grey tones of the plurality of stripes of the scanned image takes place photometrically.

7. The method according to claim 6 comprising, generating at least one recording of the adhesive strip and determining the grey tones on the basis of the at least one recording.

8. The method according to claim 7, wherein several recordings are generated from the adhesive strip and in order to improve the sharpness of depth are superimposed to form a new representation.

9. The method according to claim 1, wherein the average grey tones of at least 20 stripes are determined.

10. The method according to claim 1, wherein the grey tone limit value is 10%-40% of the value range from minimum grey tone up to a maximum grey tone.

11. The method according to claim 1, wherein for the coated flat product the grey width and/or the representative grey tone is recorded depending on an iron content of the coating.

12. The method according to claim 11, wherein the iron content is determined on the basis of the determined dependence of the grey width and/or representative grey tone on the iron content, as well as on the basis of the determined grey width and/or the representative grey tone.

13. The method according to claim 11, wherein on the basis of the determined dependence of the grey width and/or representative grey tone on the iron content for different grey tone limit values, a grey tone limit value is specified for the determination of the grey width and/or the representative grey tone.

14. The method according to claim 11, wherein for specific coated flat products, for which the grey width and/or the representative grey tone is determined, additionally the iron content of the coating is determined, and wherein, based on the determined dependence of the grey width and/or representative grey tone on the iron content, a characteristic value is determined for a correlation of additionally determined pairs of values with the determined dependence of the grey width and/or representative grey tone on the iron content.

15. The method according to claim 14, wherein the characteristic value for the correlation is used for the purpose of quality assurance with regard to the determination of the abrasion properties of a coated flat product.

16. A device for determining the abrasion properties of a coated flat product comprising:
   a detection unit configured to scan an adhesive strip and/or a representation of an adhesive strip to generate a scanned image; and
   a determination means configured to measure an average grey tone of each of a plurality of stripes of the scanned image, each of the plurality of stripes being oriented crossways to a width of the abrasion mark.

17. The device according to claim 16 comprising, a generating means configured to generate a grey tone pattern on the basis of the average grey tones of the plurality of stripes of the scanned image and a determination means configured to determine the grey width and/or the representative grey tone on the basis of the grey tone distribution.

18. The device according to claim 17, wherein a limit value determining means is configured to determine a grey tone limit value on the basis of the grey tone pattern.

19. The device according to claim 16, wherein at least one digital camera is configured to record at least one recording from the adhesive strip.

* * * * *